(12) United States Patent
Haussmann

(10) Patent No.: US 7,025,061 B2
(45) Date of Patent: Apr. 11, 2006

(54) CUSTOMIZED PASSIVE HEARING PROTECTION EARPLUG, USE OF THE SAME AND METHOD FOR MANUFACTURING THE SAME

(75) Inventor: Mathias Haussmann, Zurich (CH)

(73) Assignee: Phonak AG, Staefa (CH)

( * ) Notice: Subject to any disclaimer, the term of this patent is extended or adjusted under 35 U.S.C. 154(b) by 0 days.

(21) Appl. No.: 10/925,145

(22) Filed: Aug. 25, 2004

(65) Prior Publication Data

US 2006/0042640 A1    Mar. 2, 2006

(51) Int. Cl.
*A61F 11/00*    (2006.01)

(52) U.S. Cl. .................. 128/864; 181/130; 181/135

(58) Field of Classification Search ............. 128/864, 128/865, 866, 867; 181/128, 129, 130, 134, 181/135
See application file for complete search history.

(56) References Cited

U.S. PATENT DOCUMENTS

| | | | |
|---|---|---|---|
| 4,537,187 A * | 8/1985 | Scott | 128/864 |
| 5,763,503 A | 6/1998 | Cowperthwaite et al. | |
| 6,148,821 A | 11/2000 | Falco | |
| 6,533,062 B1 | 3/2003 | Widmer et al. | |
| 2003/0133583 A1 | 7/2003 | Widmer et al. | |

FOREIGN PATENT DOCUMENTS

| | | |
|---|---|---|
| DE | 41 19 615 A1 | 1/1992 |
| DE | 101 58 649 A1 | 6/2003 |
| EP | 0 590 698 A2 | 4/1994 |

* cited by examiner

*Primary Examiner*—Henry Bennett
*Assistant Examiner*—Camtu Nguyen
(74) *Attorney, Agent, or Firm*—David S. Safran

(57) ABSTRACT

The invention relates to a passive hearing protection earplug for being worn at least in part in the ear canal (12) of a user, comprising a hard shell (20) having an elasticity of from shore D 85 to shore D 65 and pulling means (26) which are adapted for being manually operated by the user and which are provided at the outer end of said shell, said shell having an outer surface individually shaped according to the measured inner shape of the user's ear canal and outer ear (18). The shell has a size and an outer shape which are adapted to enable said shell to be manually moved, by seizing the pulling means, from a sound attenuation position into a communication position from which it is automatically returned into the attenuation position by elastic forces exerted by deformed parts of the user's ear canal and concha upon release of the pulling means. The invention also relates to a use of such an earplug and a method for manufacturing such an earplug.

19 Claims, 3 Drawing Sheets

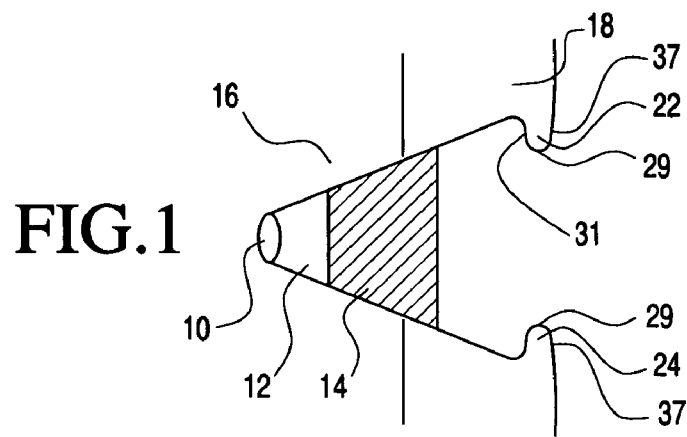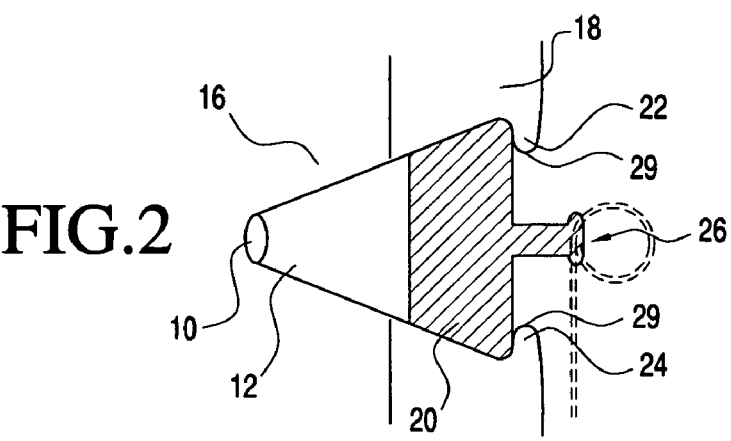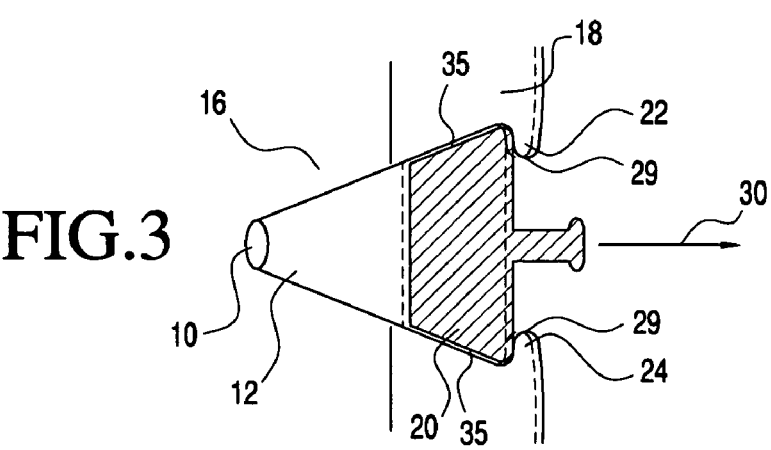

CUSTOMIZED PASSIVE HEARING PROTECTION EARPLUG, USE OF THE SAME AND METHOD FOR MANUFACTURING THE SAME

BACKGROUND OF THE INVENTION

1. Field of the Invention

The present invention relates generally to a customized passive hearing protection earplug, a use thereof and a method for manufacturing such an earplug.

2. Description of Related Art

Environmental sounds are typically composed of a mixture of various sound wave frequencies having varying intensities. It is well documented that repeated or prolonged exposure to sounds of sufficiently high sound pressure level will cause temporary or permanent hearing loss, i.e. can damage the auditory organ and cause serious hearing problems, including deafness. Harmful noise such as caused by explosions or bursts are often comprised of a mixture of sound wave frequencies of varying intensity. These disturbing frequencies are in both the high and low frequency bands and have intensity sufficient to cause hearing problems. Individuals who are frequently exposed to such disturbing and sometimes dangerous frequencies and intensities run the risk of incurring such injuries as hearing loss or even deafness. These individuals include workers at demolition or construction sites, operators of heavy, noisy equipment and those in active military service. Ear (i.e. hearing) protection is needed to prevent a loss in hearing acuity and the gradual increase in the threshold of hearing resulting from extended exposures to loud noise.

A large part of the population is exposed to hazardous noise from time to time. This can be at work, whilst traveling, during leisure activities or at home. The exposure can lead to permanent hearing loss, distract people's attention from other hazards or simply cause stress. In order to prevent both accidents and permanent hearing damage, hearing protection devices (HPDs) have been provided in many styles and over many years. It started with the earmuff which is still very relevant and addresses very noisy environments (e.g. airports, construction, shooting) or complex working/communication situations (e.g. fighter pilots). Over the years development of biocompatible soft materials has enabled soft earplugs in different styles and colors as well as recent development of "one fits many" standard semi-soft earplugs in silicon-rubber type materials. For severe situations even the combination of an earmuff and an "in-the-ear" HPD is required to achieve desired attenuation. The physical limitation of hearing protection based on ear worn devices is defined where bone-conduction (body acoustics) becomes dominant at around 40 dB attenuation.

A common disadvantage of the above mentioned HPD styles is wearing discomfort. In case of the earmuffs, they are large which creates difficulties in combination with other head worn gear and they "close off" the ear too much for most applications. The in-the-ear styles mentioned are devices made to fit "the average" ear in one way or the other. Either the fit is provided by softness of the material which leads to undefined device insertion and undefined attenuation, or the fit is provided by standard shaped structures intended to block off the ear canal. In both cases the flat distribution of the individual shape of the outer ear and the ear canal leads to bad fit, pressure points in the ear and undefined positioning of the device.

To address this wearing comfort issue, in-the-ear hearing aid technology has been applied making customized ear molds with passive acoustical filter. These are long lasting devices with good wearing comfort. However, this customization process is traditionally a very manual process creating varying results over time, low reproducibility and the quality is very operator skill dependent.

In order to overcome all of the above mentioned disadvantages a novel technique is proposed. The basic idea is to use rapid prototyping technology in a manufacturing environment as described, for example, in U.S. Pat. No. 6,533,062 B1 or U.S. 2003/0133583 A1. This technique is successfully being used in hearing aids and can be applied in a similar fashion for HPDs. By doing this, a whole new range of features and functions become feasible for HPDs.

The idea to use rapid prototyping technology, such as layer-by-layer laser sintering, in manufacturing shells, primarily for hearing aids, is described, for example, in U.S. Pat. No. 6,533,062 B1 or U.S. 2003/0133583 A1.

Passive hearing protection devices (HPDs) allowing controlled sound attenuation exist in several forms.

In spite of a certain frequency dependant sound amplitude damping achieved by some known passive HPDs, it is a fundamental property of all these devices that a higher sound attenuation of a hearing protection device will reduce the communication ability with the surroundings. The attempts of the prior art to solve this problem, namely to configure the frequency selective sound attenuation such as to retain a high dynamic in speech or voice frequencies, have failed because of the stringent requirements set up by the high noise concentration at certain working places and in the military area, for example, so that the worker, employee or soldier must temporarily remove the hearing protection device if he wants to hear persons talking to him.

U.S. Pat. No. 6,148,821 discloses a selective non-linear attenuating earplug consisting of a shell and a noise attenuation button. The button comprises a hollow stem which is inserted into a mating cylindrical outer opening of the shell. The hollow stem and the cylindrical wall of the outer opening of the shell both have a radially extending hole, which may be aligned by rotating the stem relative to the shell. The distal end of the hollow stem is provided with a sound attenuation filter connecting the interior of the hollow stem with a sound bore within said shell communicating with the user's ear canal. When the two holes are aligned, sound may enter through the opening into the interior of the hollow stem, pass through the filter and reach, attenuated by the filter, the ear canal. However, this approach does not afford non-attenuated sound communication and lacks convenient and safe operation by the user, since the button has to be reset manually and the button has to be rotated.

Further, active hearing protection devices are generally known which include a microphone, an audio signal processing unit, such as an amplifier, and a speaker for frequency-selective or temporary by-passing of the acoustic attenuation filter function provided by the earplug, for example, in order to enable acoustic communication with other persons in noisy environments.

Hearing protection earplugs having a customized shell are known, for example, from U.S. Pat. No. 6,533,062 B1. For manufacturing customized earplugs first the inner shape of the user's outer ear and ear canal is measured, for example by three-dimensional laser scanning or by forming an impression of the ear which subsequently undergoes three-dimensional (3D) laser scanning. The desired outer shape of the shell is determined from the measured shape of the user's ear for achieving optimized fit within the ear canal and outer ear. The shell can be produced by an incremental build-up process such as layer-by-layer laser sintering of a powder material, whereby a relatively hard shell is achieved which has an optimized fit within the user's ear.

It is an object of the invention to provide for a passive hearing protection earplug, which is adapted for enabling acoustic communication of the user with other persons without the need to remove the earplug from the ear, while nevertheless maintaining a simple construction of the earplug. It is a further object of the invention to provide for a use of such an earplug and to provide for a method for manufacturing such an earplug.

SUMMARY OF THE INVENTION

These objects are achieved by a passive hearing protection earplug as defined in claims 1, 2, 3 and 12, a use as defined in claims 13, 14 and 16 and a manufacturing method as defined in claims 17, 18, 19 and 20.

The invention is beneficial in that, by individually shaping the outer surface of the shell such that it is held, at its outer end, by at least part of the inwardly oriented surface of the rim of the user's cavum of concha within the user's ear canal in such a manner that it can be moved outwardly or tilted in such a manner that a communication position of the earplug with very low attenuation is achieved, while the earplug is automatically forced back into the close fitting attenuation position by elastic forces exerted by the outwardly deformed rim of the user's cavum of concha and/or by the radially deformed ear canal, the earplug enables to achieve a communication position by simple manual action on the pulling means provided at the shell, from which position the earplug is automatically returned into the attenuation position by elastic forces exerted by the deformed ear on the shell when the pulling means are released. In particular, such temporary communication function is achieved without any complex internal structures of the earplug, such as active units or a communication button, being necessary.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 1 is a schematic longitudinal cross-sectional view of the user's ear canal and outer ear with a conventional earplug inserted into the ear canal;

FIG. 2 is a view like FIG. 1, with an earplug according to the invention having been inserted into the user's ear canal, with the earplug being shown in its attenuation position;

FIG. 3 is a view like FIG. 2, with the earplug being shown in its communication position;

According to FIG. 1 a human ear comprises an ear canal 12 which is closed at its distal end by the ear drum 10 and which extends outwardly, i.e. at its proximal end, into the concha 18. The inner (distal) part of the ear canal 12 is surrounded by skull bone 16, while the concha 18 consists of cartilaginous tissue which is relatively resilient. At its outer end, the concha 18 comprises regions which are labeled tragus and antitragus and which are arranged opposite to each other. These regions are designated by 22 and 24, respectively, in the figures.

Figure 4:
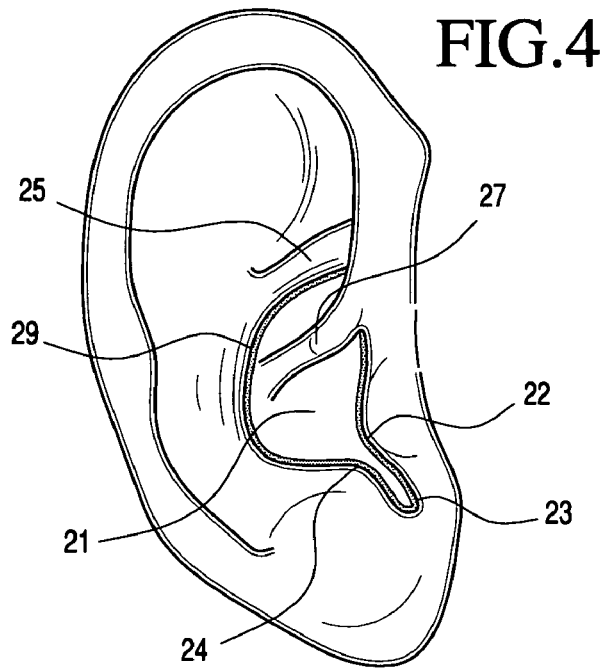
FIG. 4 is a plan view of an outer ear without an earplug.

FIG. 4 shows a plan view of the outer ear anatomy which includes the tragus 22, antitragus 24, the cavum of concha 21, the intertragic notch 23 located between the tragus 22 and the antitragus 24, the anti-helix 25 and the crus of helix 27. The cavum of concha 21 forms a pitch-like recess within the concha and is surrounded by a rim 29 (dashed line in FIG. 4) which comprises the tragus 22, the intertragic notch 23, the antitragus 24 and the anti-helix 25. The crus of helix 27 extends as a land into the cavum of concha 21.

As can be seen in FIG. 1, the rim 29 defined an undercut region in the concha 18, i.e. the rim 29 comprises inwardly (distally) oriented surfaces 31.

FIG. 1 shows a conventional customized hearing protection earplug 14, which is inserted, in the usual manner, as deeply into the ear canal 12 as possible in order to achieve maximum sound attenuation.

FIG. 2 shows an example of an earplug according to the invention when having been inserted into the ear canal 12 and the concha 18 in its sound attenuation position, with no external forces acting on the earplug 20.

The earplug 20 is a customized earplug with a hard shell having an elasticity from shore D85 to shore D65. Before manufacturing the earplug 20, the inner shape of the user's ear canal 12 and the concha 18 is measured, for example, by three-dimensional laser scanning or by forming an impression which subsequently undergoes three-dimensional laser scanning. From this data, the desired appropriate outer shape of the shell of the earplug 20 is determined by a computer model. Finally, the shell of the earplug 20 is produced by an additive build-up process (also known as "rapid prototyping"), for example, layer-by-layer laser sintering of a powder material, e.g. polyamide powder (also known as "selective laser sintering"), with an individual outer shape corresponding to the calculated shape. Such manufacturing processes are described, for example, in U.S. Pat. No. 6,533,062 B1.

According to the present invention, this manufacturing method, which is known per se, is used for shaping and sizing the shell of the earplug 20 in such a manner that the earplug 20 may be moved from its attenuation position shown in FIG. 2 by outwardly pulling and/or radially tilting the earplug 20 into a communication position in which a gap is formed between the earplug 20 and the walls of the ear canal 12 for drastically reducing the sound attenuation compared to the attenuation position. The earplug 20 is shaped and sized such that it is automatically returned from the communication position into the attenuation position by elastic forces exerted by the elastic parts of the concha 18 which are deformed in the communication position, as will be explained later in detail.

According to FIG. 2 the earplug 20 is designed such that, in its sound attenuation position, it tightly fits within at least the outer portion of the ear canal 12 and within at least part of the user's concha 18 and to tightly contact at least part of the inwardly oriented surfaces 31 of the rim 29 of the concha 18, when no external forces are present.

Figure 5:
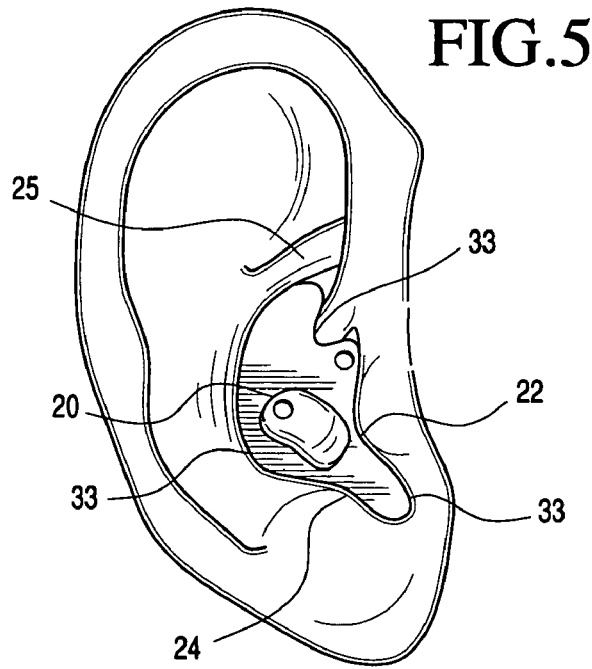
FIG. 5 is a view like FIG. 4, with an earplug according to the invention having been inserted in the ear canal and the concha.

As shown in FIG. 5, the earplug 20 in the sound attenuation position almost completely contacts the concha 18, in particular the cavum of concha 21. Preferably, it contacts at least one half of the concha 18. According to FIG. 5, in the attenuation position the earplug 20 contacts most of the rim 29 (see solid line 33 in FIG. 5).

As seen in FIG. 5, the size and shape of the outer part of the earplug 20 is selected such that the shell tightly contacts, in the attenuation position, the outwardly oriented surface of the inner crus of helix 27, whereby enhanced retention of the earplug in the concha 18 is achieved. As can be further seen from FIG. 5, the size and outer shape of the outer part of the shell of the earplug 20 is selected such, that in the sound attenuation position, the shell dos not contact the outwardly oriented surface 37 of the rim 29.

The earplug 20 is provided at its outer end with pulling means 26 which may comprise a handle (see FIG. 5), a button (see FIGS. 2 and 3), a ring or a cord (shown in FIG. 2 by dashed lines). The pulling means 26 are provided for axially outwardly pulling the earplug 20 into a communication position as shown in FIG. 3, whereby the outer end of the earplug 20 elastically deforms the undercut region of the concha 18, i.e. the inwardly directed surfaces 31 of the rim 29 experience an outwardly directed force exerted by the earplug 20 due to the axial forces pulling at the pulling means 26, whereby the rim 29, at least in the portions in close contact with the earplug 20, is outwardly deformed (this is shown in FIG. 3 for the tragus 22 and the antitragus 24, with original positions of the rim 29 and the earplug 20 being indicated by dashed lines).

By the outward movement of the earplug 20 the outer surface of the earplug 20 is at least in certain parts released from the tight contact with the wall of the ear canal 12 and the concha 18, whereby a gap 35 is formed between the earplug 20 and the wall of the ear canal 12 and the concha 18, said gap providing for a sound communication between the environment and the distal end of the ear canal 12. It is to be understood that in practice, due to the complex anatomy of the concha 18 and the ear canal 12, the communication gap 35 may have a complex geometry.

The earplug 20 is held in the communication position of FIG. 3 by continuous manual pulling at the pulling means 26 in the direction of the arrow 30 as long as a communication situation is desired by the user. The pulling forces applied at the pulling means 26 are low enough to prevent complete removal of the earplug 20 from the ear canal 12, i.e. in the communication position the outer end of the shell of the earplug 20 does not pass outwardly beyond the rim 29.

The earplug 20 is pulled outwardly at least so far that the sound attenuation, averaged over the audible frequencies, is less than 10 dB in the communication position of the earplug 20 in order to allow for a sufficiently unobstructed communication.

In practice, such conditions will be achieved if the plug 20 is outwardly pulled by a distance between 0.5 mm and 5 mm in its communication position relative to the attenuation position in which no external forces act on the earplug 20. In order to achieve such movement into a communication position having sufficiently low attenuation, it will be necessary to apply an outwardly directed pulling force of at least 0.3 N, preferably at least 0.5 N. The maximum pulling force is determined by the force which is necessary to completely remove the earplug 20 from the concha 18. In practice, the maximal pulling force is preferably below 1.5 N. These values are typical values. In practice the individual values will have some statistical spread.

Once the pulling means 26 are released by the user, the earplug 20 will be automatically returned to the attenuation position of FIG. 2 by the elastic forces exerted by the outwardly deformed rim 29, in particular of the outwardly deformed tragus 22 and antitragus 24, on the outer end of the shell of the earplug 20. In practice, the major part of these elastic return forces will be exerted by the outwardly deformed tragus 22 and antitragus 24.

The primary aspect of the present invention is that the earplug 20 is shaped in such a manner that it enables to be pulled outwardly from the attenuation position to some extent into a communication position in which the earplug 20, however, still is retained by the concha 18 in such a manner that the earplug 20 returns automatically due to the elastic forces created by the deformation of the concha 18 in the communication position, if the external pulling forces acting on the pulling means 26 are relieved. Thereby the hearing protection earplug 20 is provided in a very simple manner with a communication function in which the attenuation provided by the earplug is low, without the need to completely remove the earplug 20 from the ear or to provide the earplug 20 with internal means for by-passing the acoustic attenuation provided by the earplug 20 in its attenuation position.

In other words, the earplug 20 has to be shaped in such a manner that it can be pulled out sufficiently far for enabling a communication function but nevertheless it has to be retained with sufficiently large elastic forces in this position for enabling automatic return into the attenuation position.

A further aspect of the present invention resides in the fact that, in addition or alternatively to axially pulling at the earplug 20 for moving it into the communication position, it is possible to radially pull at the pulling means 26 in the sound attenuation position of the earplug 20 in order to slightly tilt the earplug 20 within the ear canal 12 and concha 18 in order to create a communication gap between the outer surface of the earplug 20 and the wall of the ear canal 12 and concha 18. Thereby the wall of the ear canal 12 and the inner part of the concha 18 will be radially deformed by the tilting movement of the earplug 12, while part of the rim 29 will be deformed outwardly (if the radial pulling forces act downwardly on the pulling means 26 in FIGS. 2 and 3, the upper part of the rim 29, i.e. the tragus 22, will be deformed outwardly by the tilting movement of the earplug 20, while, if the pulling force would act upwardly, the lower part of the rim 29, i.e. the antitragus 24, would be outwardly deformed). Also in this case, the elastic forces created by the radially deformed part of the ear canal 12 and the concha 18 and the outwardly deformed part of the rim 29 would act on the earplug 20 in order to return it automatically to the sound attenuation position, if the pulling forces are relieved.

The key to the following features and functions is this technology's capability to model and customize the earplug both to fit the individual shape of the ear, but also to utilize the given shape and volume for additional functionality. In some cases the processed earplug (with the mentioned rapid prototyping technology) becomes the chassis for the additional function (e.g. "RFID (radio frequency identification)", "HPD detection part", "multipurpose cord adapter") or the function is fully integrated (e.g. "intelligent HPD resonator"). The following list of functions and features indicates examples of application.

Figure 6:
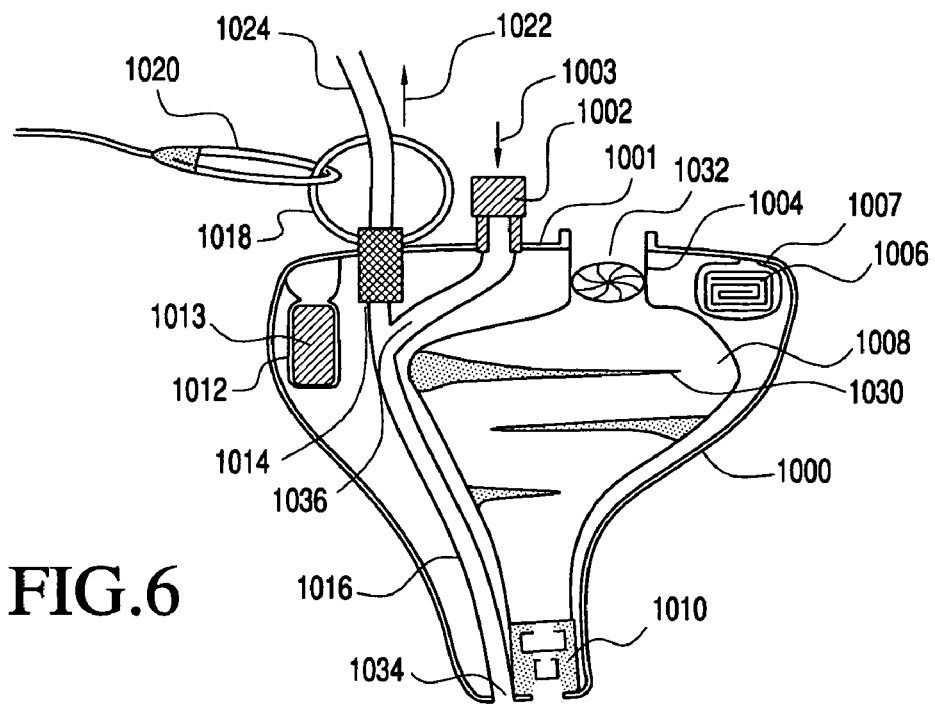
FIG. 6 is a schematic longitudinal sectional view of an example of a passive hearing protection earplug according to the invention.
Figure 7:
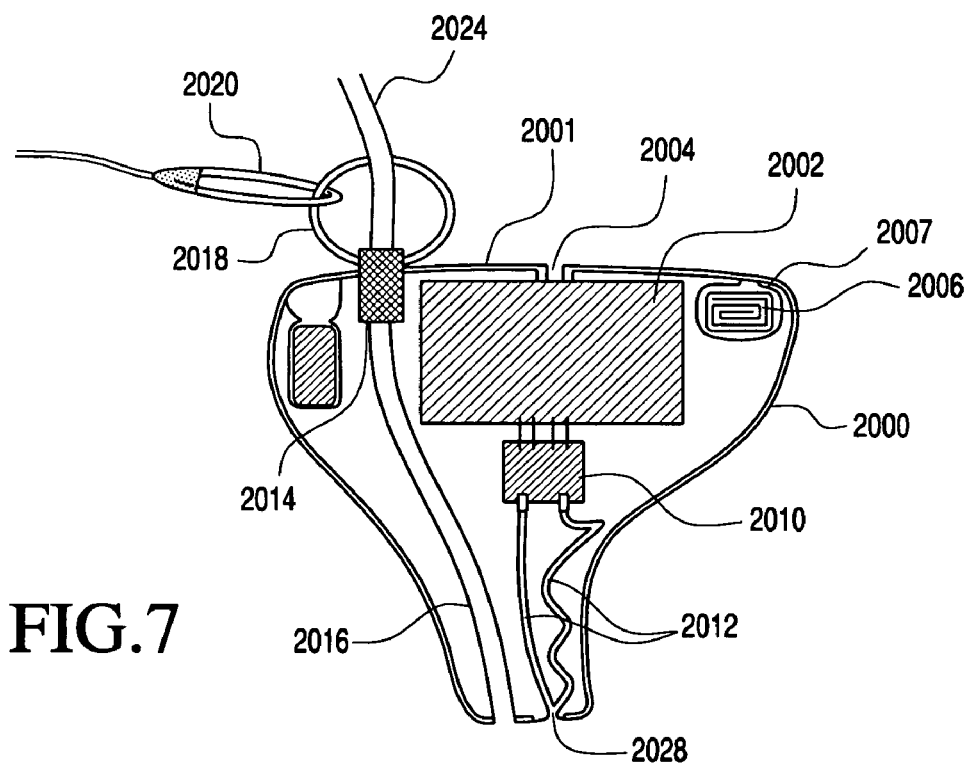
FIG. 7 is a schematic longitudinal sectional view of an example of an active hearing protection according the invention.

FIGS. 6 and 7 show an example of a passive hearing protection earplug and an active hearing protection earplug, respectively, which include the above mentioned individual outer shaping of the shell in order to enable an attenuation position and a communication position with automatic return to the attenuation position according to the invention. However, the earplugs of FIGS. 6 and 7 combine some additional features which may be advantageously implemented by manufacturing the shell of the earplug by an additive build-up process, such as layer-by-layer laser sintering. In particular, these features address functionality in addition to the individually optimized outer shape of the shell.

The earplug of FIG. 6 includes a customized hard shell 1000 with a faceplate 1001 at its outer (proximal) end. The faceplate 1001 includes an outer sound input opening 1032 provided with a mechanical peak clipper 1004, a multipurpose cord adapter element 1014 with an in-situ measuring hole for optionally connecting the measuring hole to an external measuring tube 1024 or to a plug for closing the measuring hole in the normal operation of the earplug, and a sound inlet opening which is provided with a button 1002 which is manually operable in the direction 1003 to act as an attenuation button closing the sound inlet opening or as communication button opening the sound inlet opening for sound input into a sound passage 1036 which merges at its distal end with an in-situ measuring channel or tube 1016 which is acoustically connected to the measuring hole in adapter element 1014 and which extends to an inner sound opening 1034 at the inner end of the shell 1000. The sound input opening 1032 communicates with a resonance cavity 1008 with an inner mechanical structure 1030 for frequency tuning. At the distal end of the resonance cavity 1008 a semi-integrated passive acoustic filter 1010 is provided. The tubes 1036 and 1016 are formed integral with the shell 1000. Further, also an insert cavity 1007 for a RFID (radio frequency identification device)-tag 1006 and an insert cavity 1012 for a detectable metal part 1013 are formed integral with the shell 1000. At the adapter element 1014 or at the plug for closing the measuring hole of the adapter element a cord fixation ring 1018 may be provided for fixing a neck cord 1020 at the shell 1000 for preventing loss of the earplug. The ring 1018 or the cord 1020 also may serve to manually pull the earplug in the axial direction 1022.

The earplug of FIG. 7 includes a customized hard shell 2000 with a faceplate 2001 at its outer end. The shell 2000 includes a cavity for an active unit 2002 which may comprises a microphone, an audio signal processing unit (e.g. an amplifier), a programming interface, a volume control, a push button and a battery. The unit 2002 produces an audio signal output for an output transducer unit 2010, comprising one or several speakers/receivers which are acoustically connected via sound output channels 2012 to a sound output opening 2028. The faceplate 2001 includes a faceplate opening 2004 which may serve for sound input to the microphone of the active unit 2002 and/or for access to the programming interface, the volume control, the push button and/or the battery of the active unit 2002. Similar to the passive HPD of FIG. 1, an internal in-situ measurement channel 2016 with an adapter element 2014 at the faceplate 2001 for temporarily connecting to an external measurement tube 2024, a cord fixation ring 2018, a neck cord 2020 and a cavity 2007 for a RFID-tag 2006 are provided.

The cord fixation ring 1018, 2018 and/or the neck cord 1020, 2020 may serve as the pulling means for moving the earplug into the communication position.

In the following, the additional features and their functions will be explained in more detail.

Multipurpose Cord Adapter

In order to confirm acoustical performance of an HPD, an in-situ measurement tube is implemented to allow measurement of attenuation when the individual wears the device. Naturally this tube needs to be closed off during normal operation. The core element of this tube is the faceplate component referred to a multipurpose cord adapter 1014, 2014 that embodies several functions and features: fixation of external in-situ measurement probe tube 1024, 2024, one possible holder of the cord fixation ring 1018, 2018 for the neck cord 1020, 2020, holder of an ergonomic pull means (e.g. the cord fixation ring 1018, 2018) for an inverse anatomy switch, holder of a plug for closing the in-situ tube during normal operation. If the element is made of metal it can serve as a metal component for detection purposes 1013 which in that case spares an extra insert cavity 1012. The design of the multipurpose cord adapter element 1014, 2014 is given extensive freedom (shape, material, insertion/removal concept, etc.) due to the base technology used for the faceplate portion of the earplug 1001, 2001.

Semi-Integrated Passive Filter

In passive HPDs acoustical filters mainly serve two purposes: firstly there is the defined amount of attenuation, secondly the filter can shape the frequency response of the attenuation in order to protect some frequencies while letting others through (e.g. block low frequency noise and let speech pass above 1 kHz). The proposed base technology enables both usages of predefined component placement geometries (e.g. cavities 1012 for metal component 1013 insertion) as well as semi-integration of functions where the material itself becomes part of the solution (e.g. insert cavities, acoustical filters). The semi-integrated passive filter 1010 is a structure of the second kind, where the tubes are made in shell material while the membranes are inserted components. Selection of membranes can be done to order and individual need, hence the component remains customizable. The filter must be considered and dimensioned together with other filter means like the customizable front chamber shaping structure (or resonance cavity) 1008, 1030 (Helmholtz resonator) and the mechanical peak clipper 1004.

Communication/Attenuation Button

A core function of a passive HPD is to enable temporary audio bypass for purposes like listening to speech, alarm or other desired audio signals even though they are mixed with loud noise. This is often performed by a push/return-button opening a tube either bypassing the filter of the system or leading into the in-situ measurement probe tube 1016 on the inside of the closing plug to be connected to the adapter element 1014 when the measuring tube 1024 is removed. The integration of such a device into the faceplate 1001 overcomes many drawbacks of similar standard component solutions (e.g. complex tubing, acoustical leakage). An even more integrated solution is achieved by building the switch directly into the multipurpose cord adapter core element 1014 replacing the sealing plug. If the button is made of metal it could serve as a metal piece for the detection function, thereby eliminating the need for the separate metal part 1013.

Intelligent Passive HPD

Inserting a device into the ear principally blocks the acoustical tube (ear canal) and destroys the natural outer ear amplification and frequency shaping (open ear gain, OEG). The open ear has a natural resonance in the frequency area of the most critical speech information, hence this loss is a real loss and not normally desired. The resonance frequency is given by the length of the tube; hence there is a need for compensation of the reduced length. This can be individually modeled and implemented with a defined acoustical front (outer) chamber 1008 and artificially stretched to a desired length by a mechanical means 1030 for resonance shaping directly integrated into the shell making process, possibly in combination with frequency shaping filter 1010 and means for maximum power limiting such as a mechanical peak clipper 1004.

Mechanical Peak Clipping

Many applications for HPDs experience strong variations in noise exposure over time. The extreme example is people shooting with guns (military, hunters) where speech communication in-between the actions is strongly desired and where the sound gets very loud for a short time. In active devices such conditions have been solved with so-called "peak clippers" which are fairly easy to implement in electronics and which limit the output of the device independent of the input signal while leaving the signal undistorted for normal noise levels. For a passive device this can be realized by a pressure sensitive valve 1004 opening or blocking the audio canal at the sound inlet.

Acoustical Tubing

Analog to the intelligent passive HPD acoustical shaping, several audio signal enhancements can be pursued by means of acoustical tubing for active HPD devices. Active HPDs are systems where the incoming sound picture is picked up by a transducer microphone system, processed electronically and converted back to acoustical domain by a transducer receiver (loudspeaker). Many properties and artifacts of the signal can be taken care of in the electronic domain, but some remain difficult (e.g. resonance peaks, relation direct (venting) and indirect (processed) sound) and in particular the upcoming challenge of managing wide band receivers (e.g. two-way) for high-fidelity applications. Broadband output transducers 2010 made for such applications produce multiple output signals the mixing of which becomes complex. The ability to determine the shape and length of the individual acoustic tubes 2012 and their mixing point becomes a design and modeling choice at production time. Naturally such a system can be combined with the semi-integrated passive filter mentioned earlier for further degrees of freedom.

Detectable HPD

HPDs are mostly used in industrial environments. In the food processing industry an additional requirement also affects these devices. Any foreign particle (to the food ingredients) must be detectable within the production process. For HPDs this implies that the devices need to contain a certain amount of metal to enable the detection equipment to find it if lost in the production line. Metal can be inserted into HPDs in a number of different ways: for active devices there should be enough metal in the transducers 2002, 2010 and the battery contained in 2002, hence no additional component is needed. In case of passive devices metal can be mixed into the shell base material 1000, a specific metal component 1013 can be mounted in a prepared cavity 1012, the cord adapter faceplate element 1014 can be made of metal and the button part of the on/off switch 1002 can be made of metal. In a HPD with a RFID tag, the tag itself is detectable if the equipment for detection is implemented in the production line.

HPD Wearing Compliance

Wearing of HPDs in industrial environments obliges to regulations in most countries. Assuming that the devices have the desired protective effect when they are worn (most other topics described address this very issue), the wearing itself becomes the compliance control topic. With recent developments in miniaturized RFID (radio frequency identification devices) technology, it becomes feasible to implement such devices into a customized HPD given the shell technology described. The RFID tag 1006, 2006 is inserted into a predefined cavity 1007, 2007 and when the wearer passes through gateways equipped with RFID detection systems, the positions of the two HPDs can be obtained and the control function carried out according to whether a predefined condition regarding the detected positions is fulfilled or not (e.g. separation of the HPDs according to the width of the head and height of the HPDs according to the ear height). As mentioned, the RFIDs can also serve as HPD detection devices in food production processes.

Basic Functions

Functions that conventionally are mounted components, such as a grip handle for insertion and removal of the HPD, can easily be integrated with use of the shell technology. The product design and assembly more and more becomes a software issue and the individual product is increasingly designed to order according to the specific requirements of each customer.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A passive hearing protection earplug for being worn at least in part in am ear canal of a user, comprising a hard shell having an elasticity of from shore D 85 to shore D 65 and pulling means which are adapted for being manually operated by said user and which are provided at an outer end of said shell, said shell having an outer surface individually shaped according to a measured inner shape of said user's ear canal and outer ear, wherein said shell has a size and an outer shape which are adapted to enable said shell, when said earplug is worn in said user's ear canal in a sound attenuating position in which no external forces act on said shell, to tightly fit within at least an outer portion of said user's ear canal and within at least part of said user's concha and to tightly contact at least part of an inwardly oriented surface of a rim of said user's cavum of concha including a tragus, intertragic notch, antitragus and antihelix, and which are adapted to enable said earplug, when said earplug has been pulled outwardly by external forces acting axially on said pulling means from said sound attenuation position into a communication position in which said shell is released from a wall of said user's ear canal and concha for forming a sound communication gap between said wall of said user's ear canal and concha and said outer surface of said shell, which gap extends from an environment to said user's eardrum, with said rim of said user's cavum of concha being outwardly deformed by said shell in said communication position, to return into said sound attenuating position by elastic forces exerted by said outwardly deformed rim of said user's cavum of concha on said shell, wherein said shell's size and outer shape are adapted to enable said earplug to withstand, in said communication position, external pulling forces acting on said pulling means of at least 0.3 N without being removed from said user's ear canal by said pulling forces.

2. A passive hearing protection earplug for being worn at least in part in an ear canal of a user, comprising a hard shell having an elasticity of from shore D 85 to shore D 65 and pulling means which are adapted for being manually operated by said user and which are provided at an outer end of said shell, said shell having all outer surface individually shaped according to a measured inner shape of said user's ear canal and outer ear, wherein said shell has a size and an outer shape which are adapted to enable said shell, when said earplug is worn in said user's ear canal in a sound attenuating position in which no external forces act on said shell, to tightly fit within at least an outer portion of said user's ear canal and within at least part of said user's concha and to tightly contact at least part of an inwardly oriented surface of a rim of said user's cavum of concha including a tragus, intertragic notch, antitragus and antihelix, and which are adapted to enable said earplug, when said earplug has been pulled outwardly by external forces acting axially on said pulling means from said sound attenuation position by a distance of from 0.5 mm to 5 mm into a communication position in which said shell is released from a wall of the user's ear canal and concha for forming a sound communication gap between said wall of said user's ear canal and concha and said outer surface of said shell and which gap extends from an environment to said user's eardrum, with said rim of said user's cavum of concha being outwardly deformed by said shell in said communication position, to return into said sound attenuating position by elastic forces exerted by said outwardly deformed rim of said user's cavum of concha on said shell.

3. A passive hearing protection earplug for being worn at least in part in an ear canal of a user, comprising a hard shell having an elasticity of from shore D 85 to shore D 65 and pulling means which are adapted for being manually operated by said user and which are provided at an outer end of said shell, said shell having an outer surface individually shaped according to a measured inner shape of said user's ear canal and outer ear, wherein said shell has a size and an outer shape which are adapted to enable said shell, when said earplug is worn in said user's ear canal in a sound attenuating position in which no external forces act on said shell, to tightly fit within at least an outer portion of said user's ear canal and within at least part of said user's concha and to tightly contact at least part of an inwardly oriented surface of a rim of said user's cavum of concha including a tragus, intertragic notch, antitragus and antihelix, and which are adapted to enable said earplug, when said earplug has been pulled outwardly by external forces acting axially on said pulling means from said sound attenuation position into a communication position in which said shell is at least partly released from a wall of said user's ear canal and concha for forming a sound communication gap between said wall of said user's ear canal and concha and said outer surface of said shell and which gap extends from an environment to said user's eardrum, with said rim of said user's cavum of concha being outwardly deformed by said shell in said communication position, to return into said sound attenuating position by elastic forces exerted by said outwardly deformed rim of said user's cavum of concha on said shell, wherein a sound attenuation averaged over all audible frequencies is not more than 10 dB in said communication position.

4. The hearing protection earplug according to claim 1, wherein said shell's size and outer shape is adapted to enable said shell, in said sound attenuation position, to tightly contact the outwardly oriented surface of said user's inner crus of helix.

5. The hearing protection earplug according to claim 1, wherein said shell's size and outer shape is adapted to prevent said shell, in said sound attenuation position, from contacting an outwardly oriented surface of said rim of said user's cavum of concha.

6. The hearing protection earplug according to claim 1, wherein said pulling means comprise one of a handle button, a ring and a cord for seizing said earplug.

7. The hearing protection earplug according to claim 1, wherein a major part of said elastic forces exerted by said outwardly deformed rim of said user's cavum of concha on said shell is exerted in a tragus region and an antitragus region of said rim of said user's cavum of concha.

8. The hearing protection earplug according to claim 1, wherein said shell, in said sound attenuation position, contacts at least one half of said user's concha.

9. Hearing protection earplug according to claim 1, wherein a sound attenuation averaged over all audible frequencies is not more than 10 dB in said communication position.

10. The hearing protection earplug according to claim 1, wherein said shell's size and outer shape is adapted to enable said earplug to withstand, in said communication position, external pulling forces acting on said pulling means of from 0.3 N and 1.5 N without being removed from said user's ear canal by said pulling forces.

11. The hearing protection earplug according to claim 2, wherein a pulling distance between said sound attenuation position and said communication position is from 0.5 mm to 5 mm.

12. A passive hearing protection earplug for being worn at least in part in an ear canal of a user, comprising a hard shell having an elasticity of from shore D 85 to shore D 65 and pulling means which are adapted for being manually operated by said user and which are provided at an outer end of said shell, said shell having an outer surface individually shaped according to a measured inner shape of said user's ear canal and outer ear, wherein said shell has a size and an outer shape which are adapted to enable said shell, when said earplug is worn in said user's ear canal in a sound attenuating position in which no external forces act on said shell, to tightly fit within at least an outer portion of said user's ear canal and within at least part of said user's concha and to tightly contact at least part of an inwardly oriented surface of a rim of said user's cavum of concha including tragus, intertragic notch, antitragus and antihelix, and which are adapted to enable said earplug, when said earplug has been tilted relative to said user's ear canal and concha by external forces acting radially on said pulling means from said sound attenuation position into a communication position in which said shell is partly released from a wall of said user's ear canal and concha for forming a sound communication gap between said wall of the user's ear canal and concha and said outer surface of said shell and which gap extends from an environment to said user's eardrum, with a part of said rim of the user's cavum of concha being outwardly deformed and a part of the ear canal being radially deformed by said shell in said communication position, to return into said sound attenuating position by elastic forces exerted by said outwardly deformed part of the rim of the user's cavum of concha and by said radially deformed part of said user's ear canal on said shell, wherein a sound attenuation averaged over all audible frequencies is not more than 10 dB in said communication position.

13. A use of a passive hearing protection earplug according to claim 2, comprising: inserting said earplug into said user's ear canal for reaching said sound attenuation position, manually pulling said earplug axially outwardly by a distance of from 0.5 mm to 5 mm into said communication position by seizing said pulling means, manually holding said earplug in said communication position against said elastic forces exerted by said outwardly deformed rim of said user's cavum of concha by continued seizing of said pulling means, and releasing said pulling means for returning said earplug into said sound attenuating position by said elastic forces exerted by said outwardly deformed rim of said user's cavum of concha.

14. A use of a passive heating protection earplug according to claim 1, comprising: inserting said earplug into said user's ear canal for reaching said sound attenuation position, manually pulling said earplug axially outwardly into said communication position by seizing said pulling means, manually holding said earplug in said communication position against said elastic forces exerted by said outwardly deformed rim of said user's cavum of concha by continued seizing of said pulling means with a pulling force of at least 0.3 N, and releasing said pulling means for returning said earplug into said sound attenuating position by said elastic forces exerted by the outwardly deformed rim of the user's cavum of concha.

15. The use according to claim 14, wherein said pulling force is less than 1.5 N.

16. A use of a passive hearing protection earplug according to claim 12, comprising: inserting said earplug into said user's ear canal for reaching said sound attenuation position, manually tilting said earplug into said communication position by seizing and radially pulling said pulling means, manually holding said earplug in said communication position against said elastic forces exerted by said outwardly deformed part of said rim of said user's cavum of concha and by said radially deformed part of said user's ear canal by continued seizing of said pulling means, and releasing said pulling means for returning said earplug into said sound attenuating position by said elastic forces exerted by said outwardly deformed part of said rim of said user's cavum of concha and by said radially deformed part of said user's ear canal.

17. The hearing protection earplug according to claim 2, wherein said earplug is adapted to produce sound attenuation of at least 10 db when said earplug is worn in said user's ear canal in a sound attenuating position.

18. The hearing protection earplug according to claim 3, wherein said earplug is adapted to produce sound attenuation of at least 10 db when said earplug is worn in said user's ear canal in a sound attenuating position.

19. The hearing protection earplug according to claim 12, wherein said earplug is adapted to produce sound attenuation of at least 10 db when said earplug is worn in said user's ear canal in a sound attenuating position.

* * * * *